United States Patent [19]

DellaPenna

[11] Patent Number: 5,569,831
[45] Date of Patent: Oct. 29, 1996

[54] TRANSGENIC TOMATO PLANTS WITH ALTERED POLYGALACTURONASE ISOFORMS

[75] Inventor: Dean DellaPenna, Tucson, Ariz.

[73] Assignee: The Arizona Board of Regents on behalf of the University of Arizona, Tucson, Ariz.

[21] Appl. No.: 273,538

[22] Filed: Jul. 11, 1994

Related U.S. Application Data

[63] Continuation-in-part of Ser. No. 880,915, May 8, 1992, abandoned.

[51] Int. Cl.$^6$ .............................. A01H 4/00; C12N 1/21; C12N 5/14; C12N 15/82
[52] U.S. Cl. .................. 800/205; 800/255; 800/DIG. 44; 435/172.3; 435/320.1; 435/252.3; 435/240.4
[58] Field of Search ............................... 435/172.3, 320.1, 435/252.3, 240.4; 800/205, 255, DIG. 44; 536/23.2, 23.6

[56] References Cited

U.S. PATENT DOCUMENTS

| | | | |
|---|---|---|---|
| 4,801,540 | 1/1989 | Hiatt et al. | 435/172.3 |
| 5,073,676 | 12/1991 | Bridges et al. | 800/205 |
| 5,107,065 | 4/1992 | Shewmaker et al. | 800/205 |

OTHER PUBLICATIONS

Boswell, et al., "Computational Molecular Biology Sources and Methods for Sequence Analysis (Desk Ed)", *Oxford University Press*, Oxford, pp. 170–171 (1988).
Bruinsma, et al., "Polygalacturonase Activity in the Ripening Tomato Fruit" *NATO ASI Series, Vol. H35: Cell Separation in Plants* (Osborne, et al. eds., Springer–Verlag Berlin Heidelberg (1989).
DellaPenna and Bennett, "In Vitro Synthesis and Processing of Tomato Fruit Polygalacturonase," *Plant Physiol.* 86:1057–1063 (1988).
DellaPenna, et al., "Polygalacturonase Isoenzymes and Pectin Depolymerization in Transgenic *rin* Tomato Fruit," *Plant Physiol.* 94:1882–1886 (1990).
DellaPenna and Zheng, "Purification and Cloning of the Beta–subunit of Tomato Fruit PGI," Abstract and Poster presented by ISPMB meeting in Oct. 1991.
Giovannoni, et al., "Expression of a Chimeric Polygalacturonase Gene in Transgenic *rin* (Ripening inhibitor) Tomato Fruit Results in Polyuronide Degradation but not Fruit Softening," *The Plant Cell* 1:53–63 (Jan. 1989).
Giovannoni, et al., "Polygalacturonase and Tomato Fruit Ripening," *Horticultural Review* (1990) (Manuscript).
Grierson, et al., "NATO ASI Series H35" (Osborne et al. eds), pp. 1–9.
Instruction manual for the ZAP–cDNA Synthesis Kit (Strategene)Knegt, et al., "Conversion of the Polygalacturonase Isoenzymes From Ripening Tomato Fruits," *Physiologia Plantarum* 72:108–114 (1988).
Kramer, et al., "Field Evaluation of tomatoes With Reduced Polygalacturonase by Antisense RNA," *Horticultural Biotechnology* 347–355 (Wiley–Liss, Inc. 1990).
McCormick, S., "Transformation of Tomato With *Agrobacterium tumefaciens*," *Plant Tissue Culture Manual* B6:1–9 (Kluwer Academic Publishers 1991).
Moshrefi and Luh, "Carbohydrate Composition and Electrophoretic Properties of Tomato Polygalacturonase Isoenzymes," *Eur. J. Biochem.* 135:511–514 (1983).
Pogson, et al., "On the Occurrence and Structure of Subunits of Endopolygalacturonase Isoforms in Mature–Green Ripening Tomato Fruits," *Aust. J. Plant Physiol.* 18:65–79 (1991).
Pressey, R., "Purification and Characterization of Tomato Polygalacturonase Converter," *Eur. J. Biochem.* 144:217–221 (1984).
Romano and DellaPenna, "Analysis of the Defense Response of Wild–Type and Ripening–Mutant Tomato Fruit to Pathogen Attach," Abstract presented at the ISPMB meeting in Oct., 1991.
Smith, et al., *Plant Molecular Biology* 14:369–379 (1990).
Tigchelaar, et al., "Tomato and Pepper Production in the Tropics": international symposium on integrated management practices, Taiwan (Greggs et al., Eds) pp. 123–136 (1989).
van der Krol, et al., *Plant Molecular Biology* (Abstract) 14:457 (1990).

*Primary Examiner*—Che S. Chereskin
*Attorney, Agent, or Firm*—Quarles & Brady

[57] ABSTRACT

Methods of creating transgenic tomatoes containing a lowered level of polygalacturonase isoform 1 are disclosed. The isolation of a DNA sequence encoding the polygalacturonase beta-subunit is disclosed. The beta-subunit sequence can be used to construct both sense and antisense plant expression constructions which can be transformed into tomato plants. The transgenic tomato plants have altered levels of polygalacturonase isoforms in that the level of isoform 1 is dramatically reduced. The resulting tomato fruit has a polygalacturonase activity level that is more heat labile, and thus more convenient for processing, and an increased level of soluble pectins.

24 Claims, 7 Drawing Sheets

TRANSGENIC TOMATO PLANTS WITH ALTERED POLYGALACTURONASE ISOFORMS

CROSS-REFERENCE TO RELATED APPLICATION

This application is a continuation-in-part of Ser. No. 07/880,915 filed May 8, 1992 now abandoned.

FIELD OF THE INVENTION

The present invention relates generally to transgenic plants. Specifically, the present invention relates to a transgenic tomato plant with altered levels of isoforms of the enzyme polygalacturonase.

BACKGROUND OF THE INVENTION

Polygalacturonase

In recent years *Lycopersicon esculentum*, the cultivated tomato, has become a popular system for studying fruit ripening. Tomato fruit ripening is characterized by a series of coordinated biochemical and physiological changes within the various subcellular compartments of the fruit tissue. These changes collectively contribute to the overall quality of the ripe fruit. The most obvious of the changes are alterations in fruit color, flavor, texture and resistance to certain pathogens.

One biochemical change in ripening fruit is the depolymerization and solubilization of cell wall polyuronides by the ripening-induced cell wall degrading enzyme, polygalacturonase (PG). PG activity increases dramatically during the ripening of many fruits, including tomato, and is the primary enzymic activity responsible for cell wall polyuronide degradation during fruit ripening. Reviewed in Giovannoni, et al, 1991 *Ann. Rev. Hortic Sci:* 67–103.

PG activity isolated from ripe tomato fruit is due to the presence of three structurally and immunologically-related isoforms of PG. These isoforms are termed PG1, PG2A and PG2B. (Ali, et al. *Aust. J. Plant Physiol.* 9:171, 1982). The PG2A and PG2B isoforms (45 and 46 kDa, respectively) appear well after the onset of ripening and are each composed of a single catalytic PG polypeptide differing only in degree of glycosylation. Because of the physical and biochemical similarity of PG2A and PG2B, the two isoforms shall be treated herein as a single isoform activity (the PG2 activity).

The PG1 isoform (approximately 100 kDa) is the first isoform to appear, at the onset of ripening, and is a heterodimer composed of the single catalytic PG2 polypeptide (either PG2A or PG2B) tightly associated with an ancillary cell wall glycoprotein, the PG beta-subunit. The formation of PG1 by association of the PG2 polypeptide with the PG beta-subunit protein alters both the biochemical and enzymic properties of the associated catalytic PG2 protein. The isoelectric point and pH optimum of PG1 are both a full unit lower than those of PG2. PG1 is more thermo-stable than PG2. PG1 retains complete activity after heating for 5 minutes at 65° C., a treatment that completely inactivates PG2.

In recent years, cDNA clones for the catalytic PG2 polypeptide have been identified and used to examine in detail the regulation of PG gene expression in wild-type and mutant tomato fruit (DellaPenna, et al, *Proc. Natl. Acad. Sci. USA* 83:6420 (1986). Analysis of PG2 genomic and cDNA clones has revealed that the catalytic PG polypeptide is encoded by a single gene which is transcriptionally activated at the onset of wild-type fruit ripening (DellaPenna et al, *Plant Physiol.* 90:1372 (1989). PG2 mRNA is synthesized de novo during the ripening of wild-type fruit and accumulates to high levels, accounting for greater than 1% of the mRNA mass. Ripening-impaired mutants of tomato, which are inhibited in many ripening processes including PG2 expression, have greatly reduced levels of PG2 mRNA. The severe reduction in steady-state PG mRNA levels in the mutant genotypes is due to greatly reduced transcriptional activity of the PG gene (DellaPenna, et al, 1989, supra).

The PG beta-subunit has also been studied. The levels of PG beta-subunit increase approximately 4-fold during fruit ripening (Pressey, R., *Eur. J. Biochem.* 144:217–221 (1984)) and apparently determine the amount of PG1 produced during tomato ripening. Therefore, as PG beta-subunit levels are depleted (by formation of PG1), the timing of appearance of the PG2 isoform is also controlled.

While it is clear from in vitro studies that PG1 and PG2 differ in their biochemical properties, the physiological significance of the isoforms and the role of the PG beta-subunit protein remains uncertain. From a physiological point of view, it seems likely that a cell wall enzyme like PG might be localized or its activity restricted to specific regions of the cell wall by association with an adhesion or localizing factor, such as the PG beta-subunit protein. Recent results in transgenic systems have also suggested that PG1 and hence the beta-subunit, play an important role in vivo with regard to pectin degradation and solubilization, presumably due to its association with the PG beta-subunit protein.

Pectolytic enzymes, such as PG, may have a role in plant pathogen interactions. Pathogen-derived pectolytic enzymes are thought to be important components of the mechanism by which pathogens penetrate and colonize plant tissues. Preliminary results from recently completed experiments have suggested that PG induction in transgenic mutant fruit increases colonization of the fruit by *Alternaria alternata*, a common late-season pathogen of wild-type tomato fruit to which mutant fruit are normally resistant. The apparent conferral of pathogen sensitivity to mutant fruit by the specific induction of PG expression suggests that increasing PG activity during fruit ripening may play an important role in altering the susceptibility of the fruit to pathogens.

In addition, antisense inhibition of PG expression in wild-type tomato has been correlated with a decrease in "fieldrot" during later stages of tomato ripening in the field. (Kramer, et al, 1990, Horticultural Biotechnology, pp 347–355, Wiley-Liss Inc.). Although the mechanism of PG associated alterations in pathogen susceptibility is not known, these results strongly suggest a role for PG in postharvest pathogenesis.

Tomato Processing

An important determinant of many processed tomato fruit products, including sauce, paste and catsup, is the viscosity (i.e. thickness) of the final product. One of the primary determinants of high viscosity is the presence of large, unmodified pectin molecules. Pectin is a naturally occurring plant cell wall carbohydrate polymer that is composed primarily of polygalacturonic acid residues. Maintenance of pectin integrity during tomato processing is an extremely important part of the commercial process.

An important factor in loss of pectin integrity (decrease in the polymer size and subsequent loss of viscosity) during commercial processing of tomatoes is enzymatic degradation of pectin by PG. Although some modification of pectins by PG occurs naturally during the ripening process (Della- Penna, et al, *Plant Physiology* 94:1882–86, (1990)), by far the most dramatic and commercially damaging action of PG on pectins and, hence, viscosity occurs when the tomato fruit is homogenized for processing. The PG enzyme present in the fruit has the potential to act in an uncontrolled fashion in homogenized fruit tissues and can rapidly degrade pectin polymers.

A rapid, high-temperature heat treatment is used in commercial tomato processing to destroy PG enzyme activity and thereby maintain a higher viscosity in the final product. This treatment often comprises a process known as "hot break" and is performed by the rapid heating of the tomato product to near boiling point, to inactivate the PG enzyme as rapidly as possible. The annual cost associated with the input of large amounts of energy to bring millions of tons of tomatoes to the temperature needed to rapidly inactivate PG represents a significant cost to tomato processing industries. Annual tomato production in the U.S. is approximately 6 million metric tons representing approximately 10% of worldwide production (1980 figures).

It follows that any process that would allow less energy to be used to inactivate PG in tomato products would result in substantial savings to the industry. A process that would decrease the thermal stability of the PG isoforms would therefore decrease the minimum temperature needed to heat-inactivate PG during processing. All commercially useful, non-genetically engineered tomato varieties currently on the market contain both PG1 and PG2 isoforms. Generally, 10–30% of total PG activity is PG1 in a ripe fruit. One way to decrease the thermal stability of the PG isoforms would be to inactivate or lessen the amount of PG1, the more thermo-stable PG isoform.

Antisense RNA

It has been found in both procaryotes and eukaryotes, that the production of specific endogenous proteins can be inhibited by use of an antisense RNA. An "antisense RNA" is a complementary version of a naturally occurring or endogenously produced RNA. Because of its complementary sequence, the antisense RNA will hybridize to the mRNA of the protein sought to be inhibited under physiological conditions. This hybridization prevents translation and, therefore, protein production. The duplex RNA complex thus formed is eventually degraded by appropriate cellular mechanisms, without resulting in expression of a protein. An antisense RNA can conveniently be formed for a known protein coding region by reversing the orientation of the protein coding region so that the end that is normally transcribed last is now transcribed first.

Investigators have inhibited production of the catalytic PG2 polypeptide by antisense RNA technology and have shown a greater than 92% reduction of total PG activity relative to wild-type activity levels (Kramer, et al., *Horticultural Biotechnology*, 1990, pp. 347–355, Wiley-Liss, Inc.). This reduction had significant effects on processed tomato product viscosity when the product was subjected to the normal "hot break methods. These investigators did not, however, determine which PG isoforms were produced in the transgenic fruit. One would expect that the PG2 polypeptide levels were greatly reduced and that all of the PG activity formed would be in the PG1 (heat-stable) isoform due to the presence of existing beta-subunit protein, which would not have been affected by antisense inhibition of PG2 protein.

Inhibiting the level of PG2 expression is not the equivalent of lowered levels of PG1. The reduction of catalytic PG2 polypeptide levels results in the lowering of total PG activity levels and PG2 protein levels, without affecting the formation of the heat stable PG1 isoform directly except by reducing the amount of PG2 available to form PG1. Because 100% inhibition of PG2 production has not been reported, any residual PG2 produced in PG2 antisense plants would associate with the existing beta-subunit protein to produce PG1. Heat inactivation of this remaining PG1 should still require a significant energy input.

What is needed is a transgenic tomato with lowered levels of PG1, the most heat-stable PG isoform.

SUMMARY OF THE INVENTION

The present invention is a method of creating a transgenic tomato that contains a lowered level of polygalacturonase isoform 1. The preferred method begins with the isolating of a DNA sequence that encodes at least a portion of the polygalacturonase beta-subunit. This portion is sufficient to create an antisense construct which will hybridize effectively to the mRNA for the polygalacturonase beta-subunit. A genetic construction is created from the DNA sequence in which the DNA sequence is positioned so that the antisense version of the PG beta-subunit message may be produced from the construction. This construction is then transformed into a tomato cell whereby the tomato cell produces a lowered level of polygalacturonase beta-subunit and, therefore, produces a lowered level of the PG1 isoform.

In a preferred embodiment of the present invention, the tomato plant transformation is performed by an Agrobacterium-mediated technique and the antisense construct has substantial homology to SEQ ID NO: 6.

In alternative embodiments, other genetic techniques may be used to lower levels of the polygalacturonase beta-subunit to thereby lower the level of the PG1 subunit.

The present invention is also a genetic construction comprised of (1) a promoter capable of expressing a gene in a tomato plant, (2) a sequence encoding at least a portion of the polygalacturonase beta-subunit in the antisense orientation, wherein the portion is capable of effectively hybridizing with the mRNA produced from the native gene encoding polygalacturonase beta-subunit; and (3) a 3' termination sequence.

The object of the present invention is to create a tomato plant with lowered levels of polygalacturonase isoform 1. Because polygalacturonase isoform 1 is a more heat stable form of polygalacturonase, if isoform 1 is missing, the total polygalacturonase in the tomato would be comprised of only PG2 and would be inactivated at a lower temperature than would be sufficient with a wild-type tomato whose total PG activity would consist of both PG1 and PG2 isoforms.

It is another object of the present invention to create a tomato that is potentially less susceptible to pathogens.

An advantage of the present invention is that less energy is required to inactivate the total polygalacturonase activity of the transgenic tomato described here as compared to polygalacturonase activity from wild-type tomato.

Other objects, advantages and features of the present invention will become apparent after examination of the specification, drawings and claims.

BRIEF DESCRIPTION OF THE DRAWINGS

FIG. 8 shows 63.5 C heat inactivation. FIG. 9 shows 83.5 C heat inactivation.

BRIEF DESCRIPTION OF THE INVENTION

Figure 1:
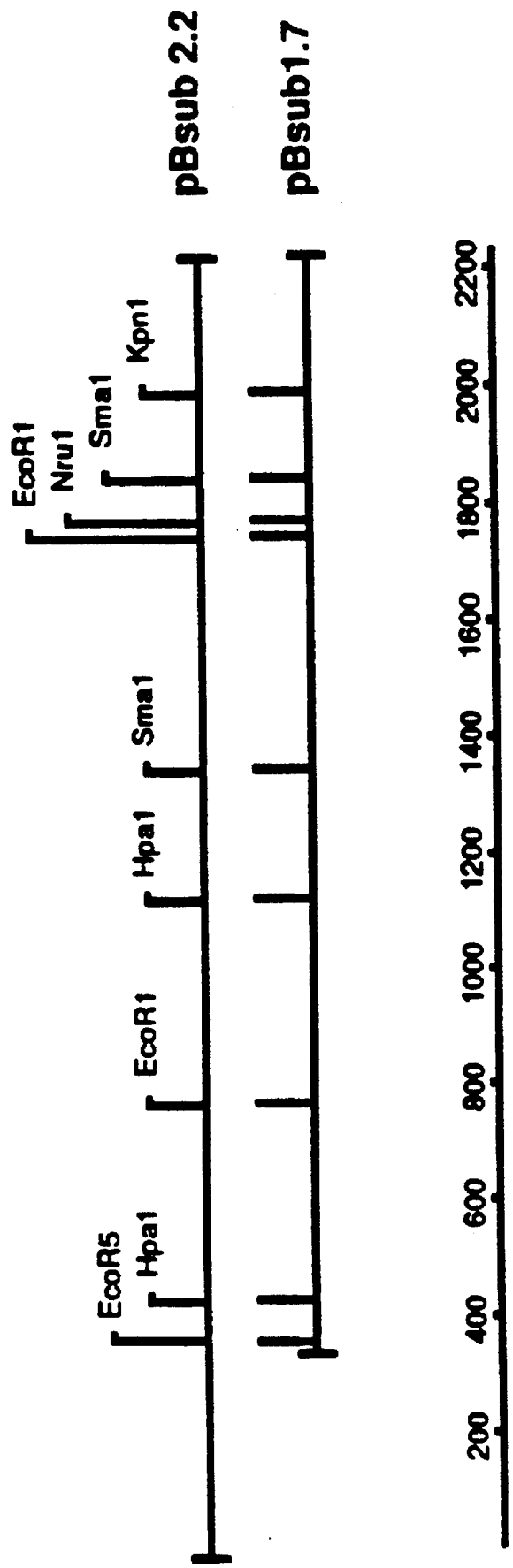
FIG. 1 is a restriction enzyme map of polygalacturonase beta-subunit cDNA clones pBsub 2.2 and pBsub 1.7.

The general strategy of the present invention is to lessen or eliminate the production of the PG1 isoform of tomato fruit by lowering the level of the beta-subunit protein by recombinant DNA techniques. The combined amount of total PG activity in the tomato fruit does not need to be changed. PG1, which is an apparently heterodimeric protein complex composed of a catalytic PG2 polypeptide and the PG beta-subunit protein, is more heat stable than the PG2 isoforms (PG2A and PG2B). The difference in heat stability between the two isoforms (PG1 and PG2) is at least 20° C. The approximate temperature of half inactivation, 5 minutes at said temperature, is about 65° C. for the PG2 isoforms and about 90° C. for PG1. Therefore, inactivating the PG1 isoform is the rate-limiting step with regard to complete heat inactivation of total PG activity during tomato processing. Elimination of beta-subunit protein production during tomato fruit development will cause the fruit to accumulate only the more heat-labile PG2 isoforms. This process will result in a commercially useful line of tomato in which higher viscosity can be maintained during processing, while simultaneously applying less heat to the tomato extracts during processing.

To lower the level of PG1 enzyme by suppressing expression of the beta-subunit in the tomato fruit, any of several strategies may be used. Among the available strategies are the use of an antisense construct, the use of co-suppression, and the use of a transposable element. The preferred methodologies are the antisense and co-suppression strategies.

The antisense strategy requires the use of at least a part of the native DNA sequence of the targeted gene to be suppressed. Once the DNA sequence of the protein coding region of the native gene is known, as it is here, it becomes possible to construct antisense DNA constructions which will produce antisense RNA in vivo in transgenic tomato to inhibit beta-subunit production. Presented below as SEQ ID NO: 6 is the near complete cDNA sequence for the tomato beta-subunit gene. From this cDNA sequence, part or all of the protein coding sequence can be reversed in orientation, inserted into expression plasmids and transformed into tomato plants. The theory of antisense gene inhibition is that as long as the antisense RNA produced is of sufficient length (generally at least about 15 bases), it will hybridize in vivo to the native mRNA, and the double stranded RNA thus formed is degraded in the cell or at least is not translated. Regardless of whether this theory is correct, the strategy works effectively in practice.

It is not necessary that the entire coding sequence of the PG beta-subunit be used in the antisense orientation. A smaller portion of the message in the antisense orientation is sufficient to hybridize to the beta-subunit mRNA and inhibit transcription. A message as small as fifteen nucleotides, if properly complementary, homologous, would be sufficient to hybridize to the gene. A sequence of in excess of twenty-five nucleotides is preferred. If an antisense RNA is sufficiently long, one or a few base pair mismatches to the target RNA will not hinder efficacy.

Standard molecular biological methods may be used to attach the antisense RNA coding sequence to suitable 5' and 3' processing sequences. A suitable promoter will be effective to promote the transcription of the antisense RNA in tomato cells. Many suitable plant promoters are known. Suitable 3' processing sequences will be effective to terminate transcription of the antisense RNA at an appropriate point. Similarly, several such polyadenylation sequences are widely known and available.

A second practical gene suppression technique is based on the phenomenon of co-suppression. This phenomenon, which is incompletely understood, occurs at some frequency in transgenic plants which have been engineered with single or multiple copies of a transgene which can be a chimeric genetic construct or additional inserted copies of a native gene in the sense orientation. In many such instances, not only does the inserted transgene fail to express, the mechanism that suppresses expression of the inserted transgene also suppresses expression of the endogenous gene copy. This phenomenon has been identified in tomato, as in Fray, *Plant Mol. Biol.* 22:589–602 (1993), and a review discussion of this technique in general can be found in Flavell, *Proc. Natl. Acad. Sci. USA*, 91:3490–3496 (1994). To use the co-suppression technique, a chimeric transgene plant expression construct is made with the tomato PG beta-subunit gene in its sense, or normal transcriptional, orientation. Regardless of transformation technique, at some repeatable frequency, the resultant transgenic plants will include some plants, or plant lines, with single, multiple, or tandem repeats of the inserted transgene and, in at least a proportion of those plants, the native PG beta-subunit expression level will be lowered.

A third strategy for lowering the effective level of PG beta-subunit expression level is based on transposable elements. Transposable elements, or transposons, are genetic elements which actuate mechanisms that move themselves to different locations in a plant genome, where they insert randomly. Transposable elements have been identified which can be transferred into foreign plant species while retaining the ability to spontaneously translocate themselves. See Chuck et al., *Plant Cell*, 5:371–378 (1993). Since transposons insert themselves randomly into the host genome, they often disrupt the expression of a gene when they insert inside of one. One could insert such a transposon into tomato, grow many plants, and search for the inevitable plant in which the transposon has translocated into the locus of the PG beta-subunit gene to disrupt its function. While laborious, this method would eventually result in a plant of the desired phenotype. In effect, this is a form of accelerated mutation and selection.

The net effect of using any of these techniques, or any other effective gene suppression technique to lower PG beta-subunit activity, is to produce a tomato plant having a novel desired phenotype. That phenotype is a tomato plant with a lowered level of expression of the PG beta-subunit protein in the fruit. The lowered level of expression of the beta-subunit does not itself effect overall levels of total PG activity in the fruit, but it will result in a proportionally lower level of PG1 as compared to PG2, which is the desired phenotype here.

It has been found here, using the preferred antisense technique, that transgenic tomato plants can be created which have dramatically decreased levels of PG1, due to the inhibition of expression of the PG beta-subunit. Useful plants can be created which have a 95% or greater reduction in PG1 activity. As is normally the case, the transgenic tomato lines created were found to vary somewhat in the extent of beta-subunit suppression, but two transgenic lines were created in which the total level of extractable PG1 activity was reduced to less than 1% of total PG activity. This phenotype stands in contrast to non-engineered, or wild-type, controls in which approximately 25% of extractable PG level is in the PG1 isoform while 75% is in the PG2 isoform. Overall levels of total detectable PG activity was not changed significantly in the transgenic tomato lines, and the fruit appeared to ripen normally.

The existence of this phenotype can readily be discovered by a heat stability test of extractable PG activity. In normal or non-transgenic tomato, heat treatment at 60° C.–80° C. will not eliminate the PG activity unless conducted for extended times (significantly in excess of 20 minutes). For transgenic tomatoes exhibiting the lowered beta-subunit characteristic, in excess of 90% of PG activity is eliminated by heating at 63.5° C. for ten minutes and an even greater extent of PG inactivation occurs after treatment at 83.5° C. in as little as five minutes. It can readily be characterized that total PG activity is substantially eliminated after ten minutes at 63.5° C. and is completely eliminated by similar treatment at 83.5° C.

The lowered beta-subunit transgenic tomato exhibits another surprising, and unexpected, characteristic. It yields a level of solubilizable pectin which is significantly increased over the wild type tomato. The increase in soluble pectin results in an increased viscosity to liquid constituents recovered from the tomato fruit. It is estimated that 5 to 10% more of the cell walls' dry weight has been solubilized in the transgenics over the controls (a 50% to 100% increase over controls). This is conventionally assayed by measuring total amount of EDTA-soluble polyuronides extracted from tomato cell wall preparations.

The genetic construction intended to suppress PG beta-subunit expression will then be placed in an appropriate expression vector for transformation into tomato plants. For an Agrobacterium-mediated transformation method, the construction should be placed in a unitary or binary Ti plasmid vector. Other methods of transformation will require different vectors. For instance, if accelerated particle-mediated transformation is desired, a simpler plasmid vector, consisting simply of the antisense construct alone, may be employed. The efficacy of an inserted foreign gene construct in transgenic plants, such as the beta-subunit suppression construct here, is independent of the method of transformation. Genetic elements to express inserted genes in plants, such as promoters and transcriptional terminators, are now well known in the art.

Set forth in SEQ ID NO: 6 below is a nucleotide sequence from a cDNA for a tomato polygalacturonase beta-subunit gene. This sequence is believed accurate as presented but, in view of the current state of the art in sequencing technology and reporting, it is not impossible that one or more minor base pair errors are present. Also, it is possible that the beta-subunit sequence may vary slightly in some tomato varieties or cultivars. The sequence information in SEQ ID NO: 6 is, however, clearly sufficient to create both effective sense and antisense transgenic plants, as demonstrated below. This sequence may also be used, as one of skill in the art may appreciate, to design a probe to recover the corresponding PG beta-subunit gene from any other tomato variety, as by hybridization assay for a genomic clone or cDNA library screening for a cDNA clone. As will be apparent below, what is required in accordance with the present invention is the suppression of PG beta-subunit activity, which can be accomplished either with SEQ ID NO: 6 or a related sequence from another cultivar.

It was also discovered that another homologous gene, possibly related to the beta-subunit gene, exists in tomato. That gene, which has been partially sequenced, is 85% homologous to the beta-subunit gene in DNA sequence. it is uncertain whether this other gene expresses in fruit or in other plant tissue. Nevertheless, the existence of this gene has not hindered the effectiveness of transgenic plants carrying either sense or antisense transgenes, as described below.

Once the vector containing the beta-subunit suppression construction is prepared, it is then necessary to obtain transgenic plants. There are many suitable methods currently used. Kramer, et al. (supra) employed an Agrobacterium-mediated method. Another transformation method that has been proven effective in tomatoes is electroporation of protoplasts. Accelerated particle transformation of tomato is also possible.

The transformed plants must be screened for the desired phenotype. This can be done by screening plants for lowered isoform levels. This can be done by testing for levels of PG1 in ripe fruit, or by conducting heating trials on tomato fruit extracts to find plants with heat labile PG activity. Both techniques are discussed below.

EXAMPLES

1. In General

We have purified the beta-subunit protein of PG1 from ripe tomato fruit and isolated cDNA clones encoding the protein. The identity of beta-subunit cDNA clones has been verified by a number of methods and the nucleotide sequence of beta-subunit cDNA has been determined. These cDNA clones will be used in the production of a genetically engineered line of tomato in which the expression of the beta-subunit will be almost entirely inhibited by an antisense gene construct.

This genetically engineered plant will contain a DNA construction capable of expressing the antisense RNA version of the beta-subunit cDNA message. Fruit expressing an antisense beta-subunit RNA would not produce the beta-subunit protein during fruit development because the antisense message would hybridize with the beta-subunit mRNA and prevent translation of the protein. The plant would therefore only accumulate the more heat-labile PG2 isoform and would not accumulate the more heat-stable PG1 isoform. Inhibiting the expression of the beta-subunit protein in tomato fruit by antisense RNA technology will modify pectin chemistry in vivo during ripening, and allow for inactivation of PG activity during commercial processing at a much lower temperature than is presently used, or much more rapidly at the temperatures presently used, thereby causing substantial savings in the cost of energy involved in production.

2. Creation of Beta-subunit cDNA Clones

A cDNA library was prepared using a commercially available kit (Stratagene, LaJolla, Calif.) with RNA obtained from mature green tomato. Mature fruit tissue was collected from greenhouse grown tomato plants and frozen with liquid nitrogen. Total RNA was extracted via the following method: Ten grams of frozen tissue was ground to a powder in liquid nitrogen with a mortar and pestle and homogenized with a polytron in 20 ml of lysis buffer [8M guanidine thiocyanate, 10 mM EDTA, 300 mM Tris-Hcl (pH 7.6), 8% b-mercaptoethanol]. Following centrifugation at 3,000 g for 10 minutes, the supernatant was filtered through miracloth and extracted twice with phenol/chloroform and once with chloroform. RNA was ethanol precipitated and the resulting pellet was washed with 3.0M sodium acetate (pH 5.5), then dissolved in 10 mM Tris, pH 7.6; 1 mM EDTA; 1% SDS and reprecipitated with 2.5M LiCl (Sambook, et al, *Molecular Cloning Manual*, Cold Spring Harbor, 1989). Total RNA was subjected to poly A+ selection as described (DellaPenna, 1986 supra).

This cDNA library was screened with probes prepared from peptide fragments of PG beta-subunit protein. The fragments were obtained in the following way: Ripe pericarp tissue was homogenized in ice-cold distilled $H_2O$ at a ratio of 1 kg fruit to 1 liter water and the resulting slurry adjusted to pH 3.0. Cell debris was pelleted by centrifugation at 10,000 g for 20 minutes, resuspended in one half volume of cold $H_2O$ at pH 3.0 and repelleted. The cell debris pellet was resuspended in cold buffer contained 50 mM sodium acetate, 1.25M NaCl (pH 6.0) and stirred for at least one hour at 4° C. The extract was centrifuged at 10,000 g for 20 minutes and proteins in the supernatant were precipitated by the addition of ammonium sulfate to 70% saturation. After centrifugation, the resulting protein pellet was resuspended in 0.125M sodium acetate (pH 6.0) and dialyzed extensively against the same buffer. The dialyzed extract was then clarified by centrifugation and applied to a CM-Sepharose column equilibrated with 0.125M sodium acetate (pH 6.0). Bound proteins were eluted by a two step gradient of 0.45M sodium acetate (pH 6.0) and 1.0M sodium acetate (pH 6.0). PG2 A and B eluted with 0.45M sodium acetate while PG1 eluted with 1.0M sodium acetate.

The 1.0M sodium acetate eluent was concentrated by ultrafiltration, dialyzed against Concanavalin A (Con-A) buffer [500 mM NaCl, 50 mM sodium acetate, 1 mM calcium acetate, 1 mM manganese sulfate (pH6.0)] and further purified by Con-A chromatography as previously described (DellaPenna, 1986 supra). PG1-containing fractions were concentrated by ultrafiltration, dialyzed against 50 mM phosphate, 200 mM NaCl, 0.1 mM DDT (pH6.0) and further purified by Mono S FPLC chromatography, Pogson et al, *Aust. J. Plant Phys.* 18:65–79 (1991).

The subunits of PG1 were separated and isolated as described (Pogson et al., 1991 supra). PG1 purification and separation of PG2 and the beta-subunit protein were followed by SDS-PAGE. Electrophoretic blotting, and detection methods for the catalytic PG polypeptide were performed as described previously (DellaPenna et al., 1986, supra). PG1 and PG2 levels during extraction and purification were determined by heat inactivation (Tucker et al., *Eur. J. Biochem.* 115:87–90, 1981) and activity staining of protein extracts separated by non-denaturing PAGE (DellaPenna, 1987 supra.).

N-terminal sequence analysis of the purified beta-subunit was performed with a Beckman 890M gas phase sequenator. Internal beta-subunit proteolytic fragments were generated by digestion with Lys-C and Glu-C endoproteases following instructions supplied by the manufacturer (Promega, Madison, Wis.). The resulting proteolytic fragments were resolved by SDS-PAGE, blotted to PVDF membranes and directly sequenced.

Two internal peptide fragments were of interest. The amino acid sequence of the Lys-C peptide was: $NH_2$-Asn-Gly-Asn-Gly-Ala-Asn-Gly-Gln-[?]-Val (SEQ ID NO: 1). The amino acid sequence of the Glu-C peptide was: $NH_2$-Ala-Asn-Ala-Gly-Asp-Gln-Tyr (SEQ ID NO: 2). The underlined portion of these sequences indicates the sequence from which a nucleotide primer was constructed. These nucleotide primers are presented at SEQ ID NO: 3 (for the Lys-C primer) and 4 (for the Glu-C primer).

These degenerate oligonucleotides were used for library screening and PCR-based MOPAC generation of cDNA probes. One microgram of poly (A)+RNA from immature green, mature green, turning and fully ripe tomato pericarp tissues was used in PCR-based MOPAC reactions. A Not I primer-adaptor (Promega, Madison, Wis.) was used as a primer for first strand cDNA synthesis. Subsequent PCR amplification cycles utilized a Not I adaptor as the 3' primer and a degenerate 5' primer (SEQ ID NO: 4), derived from the Glu-C beta-subunit protease fragment. Amplified products were electrophoresed, blotted to nylon membranes and probed with a second degenerate oligonucleotide (SEQ ID NO: 3) derived from the Lys-C beta-subunit protease fragment. The Lys-C primer recognized a 1.3 kb product generated in the MOPAC reactions. This 1.3 kb product was recovered and amplified by PCR using the Lys-C primer (5'-end) and the Not I adaptor (3'-end). This second 1.25 kb MOPAC-derived PCR product was used in conjunction with degenerate oligonucleotides for library screening and Northern analysis. Oligonucleotide 5'-end labelling and random primer DNA labelling were performed following the manufacturer's protocol (BRL, Gaithersburg, Md.).

The cDNA library contained $1.0 \times 10^7$ individual recombinants before amplification. For primary screening, replica nitrocellulose filters (25,000 pfu/plate) were probed with the degenerate 17-mer Lys-C oligonucleotide described above. Prehybridization was carried out for 4 hours at 37° C. in a solution of 6×SSC; 1×Denhardt's solution; 0.5% SDS; 0.05% sodium pyrophosphate; 100 µg/ml denatured salmon sperm DNA. Hybridization was carried out overnight at 37° C. in 6×SSC; 1×Denhardt's solution; 20 µg/ml tRNA; 0.05% sodium pyrophosphate. Following hybridization, the filters were washed twice for 5 minutes at room temperature and twice at 37° C. for 30 minutes in 5 ×SSC; 0.05% sodium pyrophosphate. A final wash was performed in 5×SSC; 0.05% sodium pyrophosphate at 40° C. for 10 minutes. The filters were exposed overnight with intensifying screens at −80° C.

Further rounds of screening were performed at low density using the PCR-generated MOPAC cDNA fragment (described above), the Glu-C oligonucleotide and a degenerate N-terminal oligonucleotide [5'-AT(AG) TCX CC(AG) CT(GA) TG(CT) TT(CT) TC (SEQ ID NO: 5)] derived from the N-terminal protein sequence. Hybridization conditions for these oligonucleotides were as described above. Hybridization conditions used with the MOPAC-generated cDNA fragments were as described by Sambook et al 1989, (supra). Following plaque purification, plasmids were rescued by in vivo excision, following the manufacture's protocol (Stratagene). Double-stranded DNA sequencing was performed.

All the beta-subunit clones we obtained have the restriction pattern illustrated in FIG. 1. We have sequenced two beta-subunit cDNA clones and fragments of 11 others. SEQ ID NO: 6 is the consensus DNA sequence we obtained from the clones. A poly-(A) tail of 35 residues was found at the end of the cDNA but has been removed from SEQ ID NO: 6.

3. Antisense Expression of the Beta-Subunit cDNA (Prophetic)

Expression of the beta-subunit protein will be modified by introducing Cauliflower Mosaic Virus (CaMV) 35S promoter driven chimeric genes containing a full-length beta-subunit cDNA in the antisense orientation into various tomato genotypes. This highly expressed constitutive promoter is widely available. Other promoters may also be utilized. The constitutive CaMV 35S promoter will be initially used for the proposed experiments because this promoter has been shown to promote high levels of protein production in most plant organs, including tomato fruit. Kramer, et al., supra.

The feasibility of reducing the expression of tomato fruit genes by antisense RNA technology has been demonstrated by Kramer, et al. (supra). A similar strategy will be employed to inhibit expression of the beta-subunit protein in transgenic tomato plants. Antisense repression of beta-subunit protein production will greatly decrease the amount of beta-subunit protein available for the formation of PG1, thereby resulting in accumulation of only the PG2 isoforms.

First, an antisense DNA construction will be created. At a minimum, this DNA construction must contain a promoter effective to promote transcription in tomato plants, an antisense version of a cDNA clone encoding PG beta-subunit, and a sequence effective to terminate transcription. Via standard molecular biological methods, the CaMV35S promoter sequence will be attached to the beta-subunit cDNA insert. The cDNA insert will be in the antisense orientation. This orientation will be accomplished by attaching the 3' end of the cDNA insert to the promoter. Preferably, the poly-(A) tail will be removed for the antisense construction with the enzyme NruI which will leave a DNA fragment of approximately 1800 bp for antisense construction (approximately 400 bp of 3' sequence plus the poly-A tail will be deleted by this method). Therefore, the antisense RNA strand will be the transcription product.

A suitable termination sequence, such as the nopaline synthase 3' terminator, will be placed downstream from the cDNA insert.

The DNA construction will be placed in an appropriate vector for plant transformation. For Agrobacterium-mediated transformation, the promoter/cDNA/terminator construction will preferably be placed in a Ti-based plasmid, such as pBI121, a standard binary vector.

In general, transformation will preferably be done with two standard Agrobacterium binary vectors: pBI121 (sold by Clontech Laboratories, Palo Alto Calif.) and pGA643 (developed by G. An at Washington State University). pBI121 contains a CAMV promoter and GUS reporter gene. The GUS coding sequence will be removed by digesting with SstI and SmaI (blunt end). The beta-subunit DNA fragment to be used will be produced by digesting with SstI (sticky end) and NruI (blunt end). The sticky/blunt ends will allow for directional cloning into pBI121 in the antisense orientation. Standard methods for cutting, ligating and *E. coli* transformation will be used.

For plant transformation we will follow, in general, the methods of McCormick (1986, *Plant Cell Reporter* 5:81–84) and *Plant Tissue Culture Manual* B6:1–9 (1991) Kluwer Academic Publishers. This later reference compiles/compares various procedures for Agrobacterium-mediated transformation of tomato.

The level of beta-subunit, individual PG isozymes and overall heat stability of total PG activity as a function of time and temperature in the tomato will then be analyzed. Fruit from transgenic antisense tomatoes can be processed and heat-treated to assess levels of PG1 activity. If as the tomato pulp is heated to between 65° C. and 90° C. and PG activity is halted more rapidly than wild-type fruit, the effort would have been successful.

4. Construction of Antisense and Sense Plant Expression Constructs and Plant Transformation The beta-subunit encoding DNA sequence as set forth in SEQ ID NO: 6 below was inserted into a vector designated pBsub2.2. Copies of a plant binary vector pBI121 were purchased (Clontech). The vector pBI121 carries a plant expression construct including a plant expressible constitutive promoter, the cauliflower mosaic virus 35S promoter, followed by the coding region for the enzyme beta glucuronidase (GUS), followed, in turn, by a polyadenylation signal from the nopaline synthase gene. In essence, the GUS coding region was excised from pBI121 and replaced with the PG beta-subunit coding region in both sense and antisense orientations.

Figure 2:
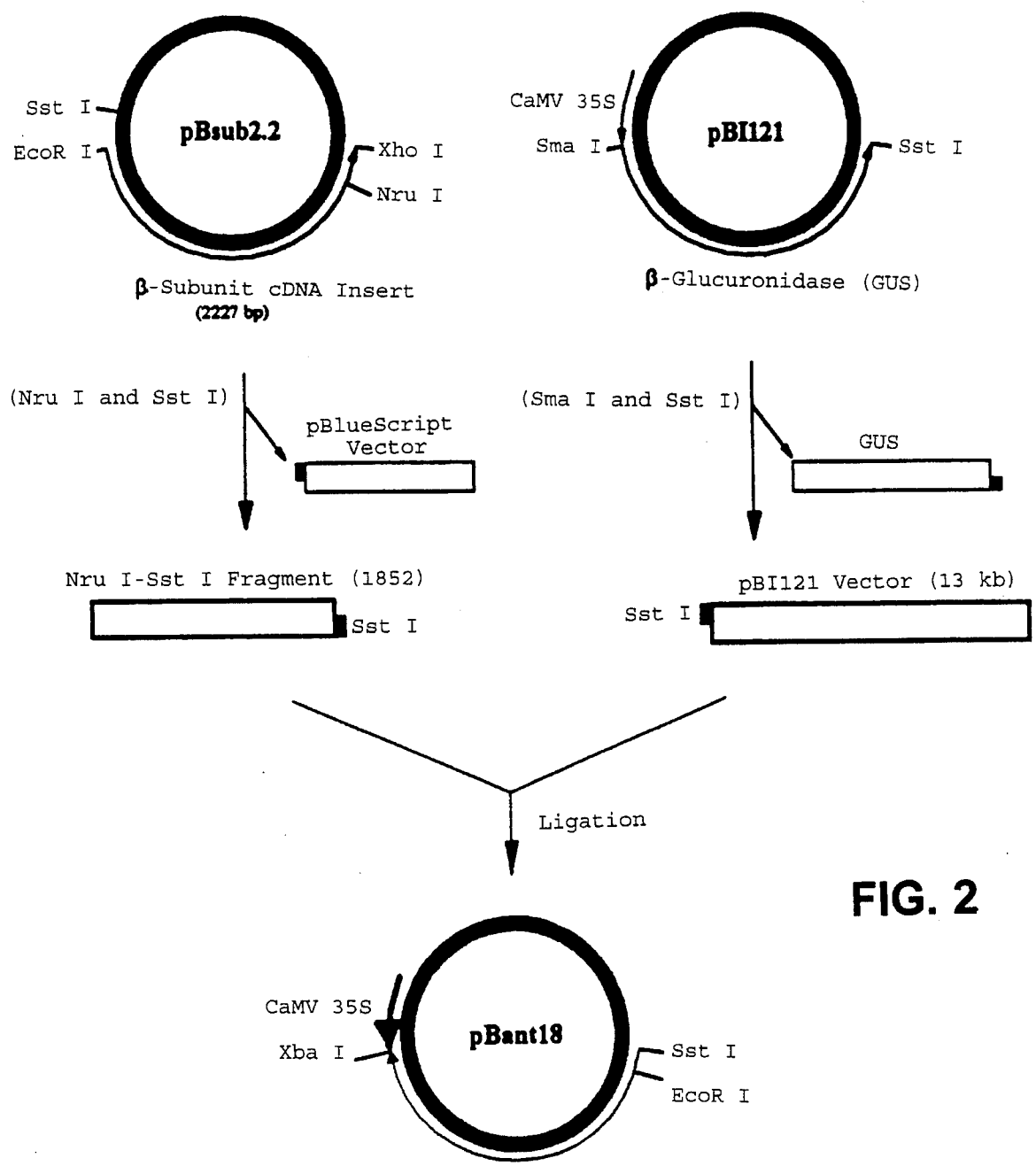
FIG. 2 is a schematic diagram illustrating the construction of plasmid pBant18.

For the antisense construction, illustrated in FIG. 2, the plasmid pBsub2.2 was digested with NruI and Sst 1. This digestion frees a 1852 base pair fragment. The NruI site is at base pair 1792 in SEQ ID NO: 6 while the SstI site in pBsub2.2 is before the cDNA insert of SEQ ID NO: 6. Separately, pBI121 was digested with SmaI (blunt end) and Sst 1 (5' overhang) to remove the GUS coding region from the vector. After size separation from unwanted fragments on agarose gels, the two desired fragments were ligated with ligase (BRL), and the resultant vectors transformed into XL-1 Blue bacteria. The antisense construction was designated pBant18.

Figure 3:
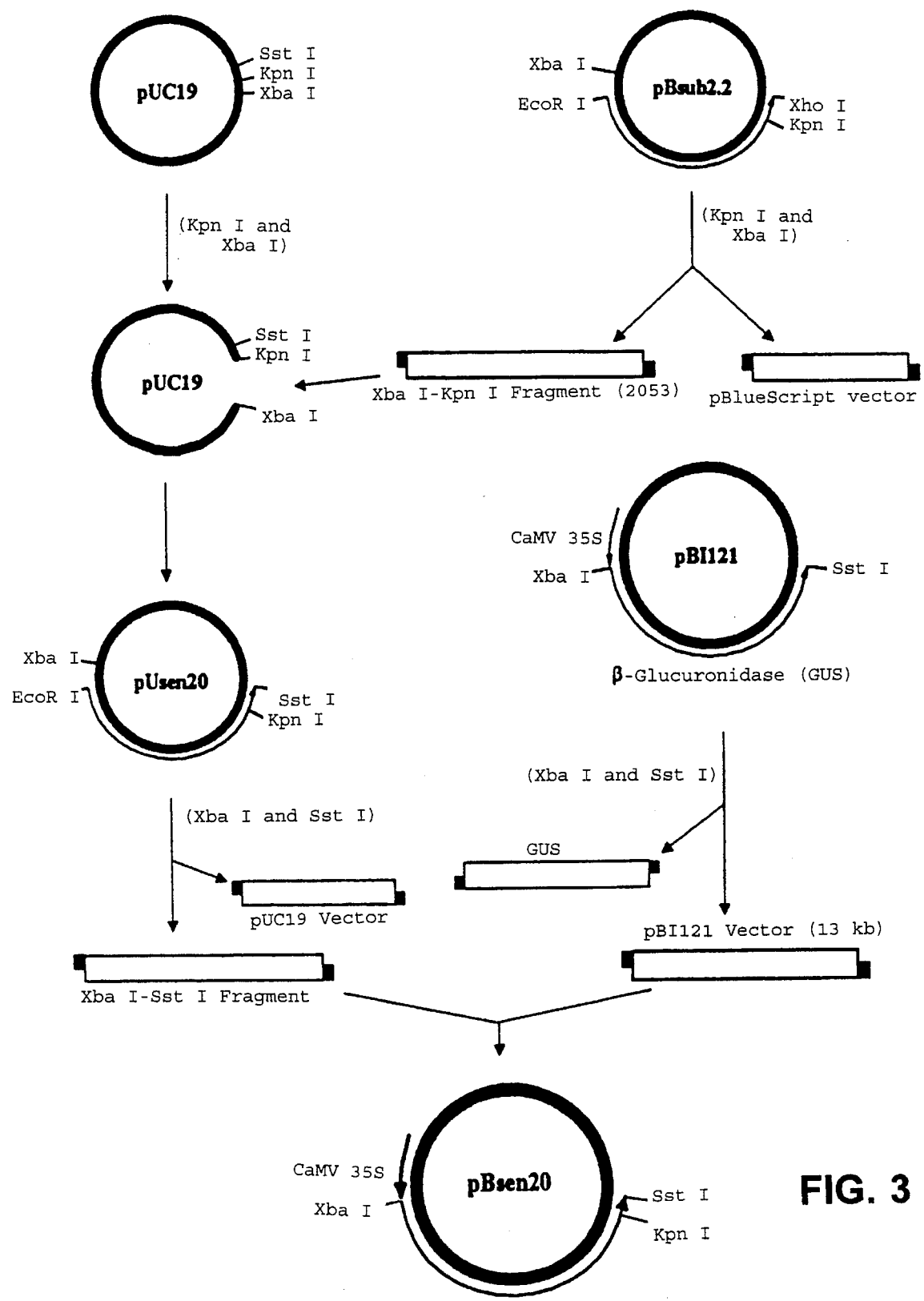
FIG. 3 is a schematic diagram illustrating the construction of plasmid pBsen20.

For the sense orientation, illustrated in FIG. 3, the pBsub 2.2 cDNA clone was digested with KpnI and XbaI, and the resulting 2053 base pair fragment was sub-cloned into the KpnI-XbaI site of pUC19, to create a plasmid designated pBsen20. The KpnI site is at base pair 2009 in SEQ ID NO: 6, and the XbaI site is again beyond base pair 1 in the host vector. The purified pBsen20 was then digested with Sst1 and XbaI, the smaller fragment was recovered from a LMA gel, and then the fragment was ligated into pBI121 previously cut with XbaI and SstI to remove the GUS coding region. The resulting plasmid, designated pBsen20 was also transformed into XL-1 Blue bacteria.

Copies of both pBant18 and pBsen20 were then transferred into *Agrobacterium tumefaciens* by the tri-parental technique. The Agrobacterium culture (LBA 4404) was grown on an M9 sucrose liquid medium without antibiotics at 28° C. Colonies of *E. coli*, (containing both pBant18 and pBsen20, as well as helper plasmid pRK2013) were streaked on LB plates under kanamycin selection (50 µg/ml) at 37° C. and then cultured in 3 ml of LB liquid medium without antibiotics. 50 µl of each of the three cultures (LBA4404, pRK2013, and the sense or antisense construction) were combined on LB plates without antibiotics to be cultured overnight at 28° C. The resultant culture was placed in 2 ml of LB liquid medium with both kanamycin (50 µg/ml) and streptomycin (250 µg/ml), and cultured overnight with shaking. Minipreps were used to verify correct constructs.

Dry tomato seeds of variety Ailsa Craig were sterilized, plated, and placed in a growth chamber for 10 to 14 days. The tops of the seedlings were cut, taking the top half of the hypocotyl as well as the cotyledons, and floated in liquid MSO. Cotyledons were cut, placed on a filter paper disk over tobacco feeder cells and cultured in a growth chamber overnight. The cotyledons were removed, plated and inoculated with the Agrobacterium harboring the genetic construction. After 48 hours of co-cultivation, the cotyledons were re-plated in D1 medium with kanamycin (25 μg/ml) and cefotaxime (100 μg/ml). Callus grew on some treated cotyledons, and the callus was sub-cultured in D2 medium with kanamycin (25 μg/ml) and cefotaxime (100 μg/ml) for shoot organogenesis. After three weeks, shoots with meristems arose. The shoots were transferred to rooting medium (MSO plus kanamycin (26 μg/ml) and cefotaxime (50 μg/ml)). The shoots were cultured in growth boxes until they were of sufficient size for transfer to the green house.

5. Characterization of Transgenic Plants and Fruit

Transgenic tomato plants were recovered containing both the sense and antisense beta-subunit transgenes. Both orientations of the beta-subunit sequence resulted in transgenic tomato lines with lowered levels of PG1 relative to PG2, even though total PG levels were unaltered. The plants appeared normal and fruit appeared to ripen normally. The best results were obtained in two transgenic lines carrying the antisense transgene, where levels of PG1 were so low as to be at the limit of detectability. In these two lines, recoverable PG1 activity represented less than 1% of the total PG activity in the fruit.

To test beta-subunit protein levels and PG isozyme levels, the fruit of transgenic and control plants was classified as mature green 42 days after pollination and the breaker stage (about 45 days after pollination) was considered to be when the first visible external coloration of the fruit appeared. At least three fruit were collected from each plant seven days after breaker stage (Br+7) and the combined pericarp tissue for the fruit for each plant were analyzed. Cell wall proteins isolated from the plants were probed immunologically for levels of beta-subunit protein and for PG2 protein as well as for PG1 isoenzyme activity. Immunoblot analysis by SDS-Page separation and probing with respective antibodies revealed that the antisense plants of lines TA8, TA9, TA10 and TA42 had less than 1% PG1 as a proportion of total PG activity while the non-transformed control exhibited about 25% PG1. PG2 levels in control and experimental lines remained, at the sensitivity of a blot analysis, similar. Further analysis confirmed that a reduction in extractable PG1 activity in 12 of 17 independently derived transgenic antisense lines was due to a concomitant reduction in detectable beta-subunit protein level. The production of lycopene in Br+7 fruit of the transgenics appeared very similar to controls indicating that the expression of the beta-subunit suppression transgene had not affected normal ripening at this stage of the fruit.

Similar results were obtained for plants carrying the sense construct. Two independently derived transgenic sense tomato lines, designated TS1 and TS4, also exhibited less than 1% PG1 level as a percentage of total PG activity in Br+7 fruit with total levels of PG and lycopene similar to controls. The two transgenic sense lines TS1 and TS4 had 3 and 2 copies of the sense transgene respectively. Also, as will be discussed with regard to antisense plants below, levels of soluble pectins were found to have increased in the transgenic fruit. The level of EDTA soluble polyuronides in the transgenic fruit was found to be slightly over 50% increased over controls. (TS1 exhibited 140 μg/mg cell wall, TS4 130 μg/mg, control 88 μg/mg).

Detailed analysis was conducted on the antisense line TA8. Two copies of the inserted transgene were found and, by analysis of selfed progeny, it was determined that the two transgenes segregated by Mendelian inheritance as a single locus. Fruit from TA8 plants were gathered at 24, 33, 37 and 42 days after pollination (dap) as well as from Br through Br+10. Western immunoblot analysis was conducted for presence of beta-subunit and PG2. Beta-subunit was first detectable in controls at 24 dap and accumulated throughout development and remained at high levels during ripening. Beta-subunit in TA8 fruit was almost undetectable at all stages of development. PG2 was detected at Br+2 in both control and transgenic fruit leading to maximal accumulation at Br+10 stage and appeared unaffected by beta-subunit antisense expression.

RNA was extracted from the same fruit tissue samples from which protein samples had been taken. The analysis of RNA levels revealed that beta-subunit RNA in controls was detectable at 24 dap, reached maximum at 37 dap and declined to undetectable levels at Br+2. In contrast, beta-subunit RNA was almost undetectable throughout TA8 fruit development and ripening.

Figure 4:
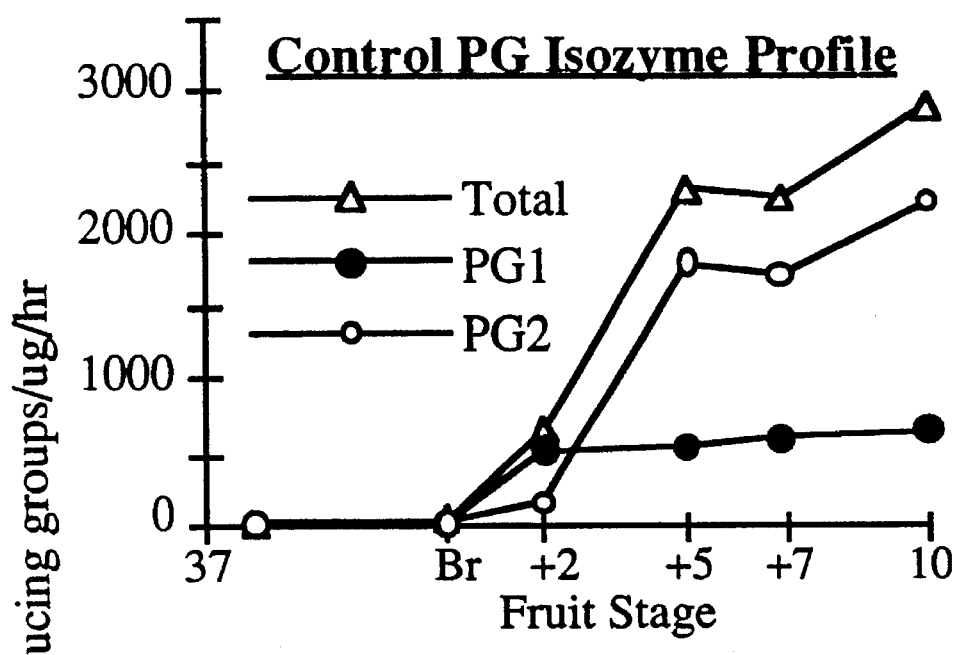
FIG. 4 is a graphical presentation of data showing relative levels of PG1 and PG2 isoforms in control plants.
Figure 5:
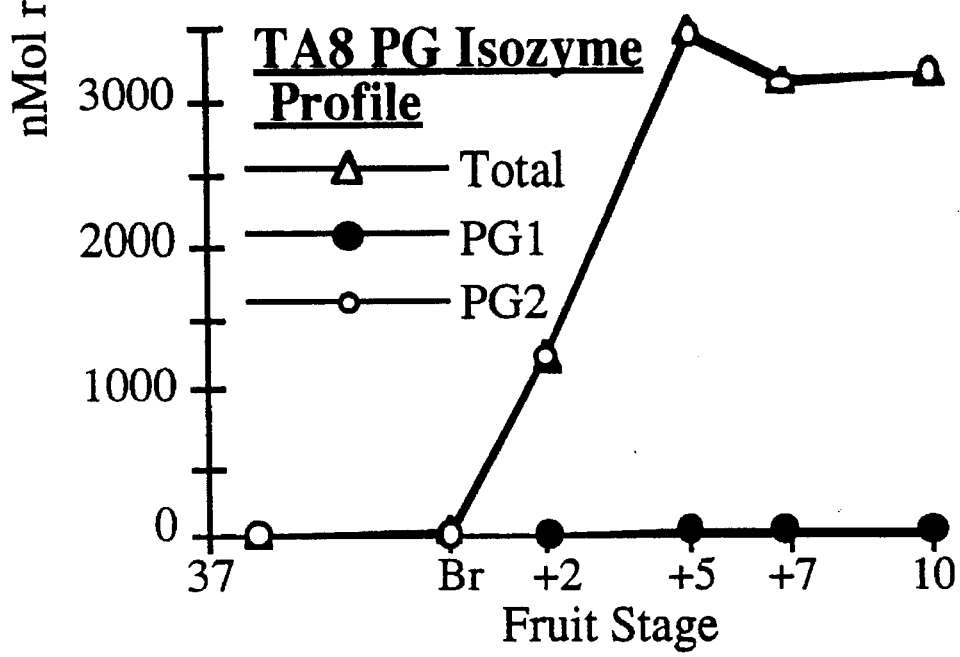
FIG. 5 is a graphical presentation of data similar to FIG. 4 for transgenic tomato line TA8.

Total cell wall protein isolated from developmental stages of mature green (42 days dap) through BR+10 fruit were also assayed by heat inactivation tests to determine relative levels of PG1 and PG2 activity. FIGS. 4 and 5 illustrate comparative results for fruit from control and TA8 plants. As ripening increases in control plants, PG1 activity increases very slightly while PG2 activity increases almost 5-fold, as illustrated in FIG. 4. In FIG. 5, the comparable illustration for TA8 fruit, it can be seen that very little PG1 activity was detected at any stage while PG2 activity continued relatively normally or at an increased level.

Figure 6:
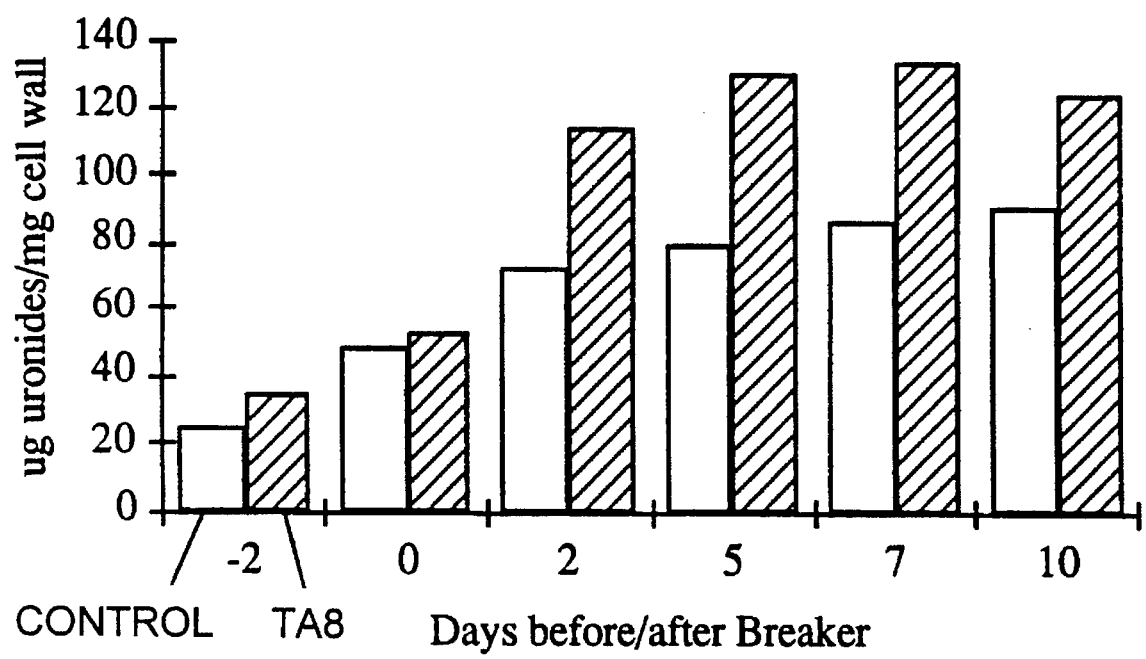
FIG. 6 is a graphical presentation of data on soluble pectins recovered from control plants compared to transgenic plants of line TA8. The open bars correspond to the control and hatched bars correspond to TA8.
Figure 7:
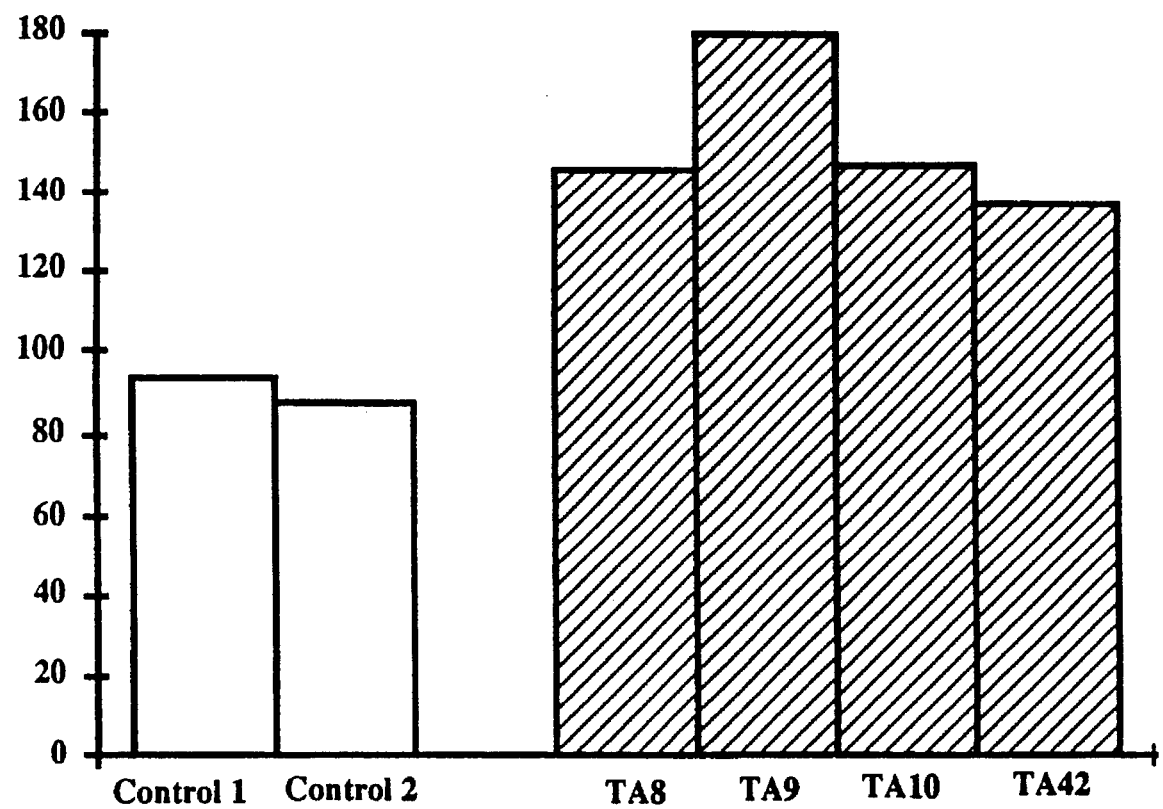
FIG. 7 is a graphical presentation of data similar to FIG. 6 comparing control plants with four transgenic plant lines.

The physical characteristics of EDTA-soluble cell wall polyuronides were also analyzed from transgenic and control tissues insofar as that analysis might shed illumination on the relative roles of PG1 and PG2 during ripening. FIG. 6 illustrates the relative levels of soluble polyuronides as analyzed from control and TA8 fruit. The yield of chelator-soluble polyuronides from ripening controls was consistent with previously published data using the same experimental protocol (i.e. DellaPenna et al. *Plant Physiol.*, 94:1882–1886 (1990), Smith et al. *Plant Mol. Biol.*, 14:369–379 (1990)). Also similarly to prior data, the majority of solubilization occurred at or near Br+2 stage in the controls where PG1 activity predominates. However, while the pattern of polyuronide solubility was similar in TA8 fruit as compared to control, the absolute amounts of polyuronides extracted throughout ripening was considerably higher. In FIG. 7, a similar graph is presented illustrating EDTA-soluble polyuronide levels at Br+7 for four transgenic lines (TA8, TA9, TA10, TA42) as compared to two controls (C1, C2). In some transgenic lines (i.e. TA9, which had three or more antisense transgenes) the level of soluble polyuronides was 200% of the levels in the controls. The average yield of EDTA soluble polyuronides in fruit from controls at BR+7 was 9% of cell wall dry weight while the four transgenic lines averaged 15.3% of the cell wall dry weight. Measurements of tomato serum viscosity verified the presence of viscosity increase that would be expected in tomato fruit extract from the presence of the higher levels of pectins. Using tomato serum, the control had a viscosity of 9.13 while the TA8 fruit serum had a viscosity of 9.84, compared to a value of 1 for water.

Figure 8:
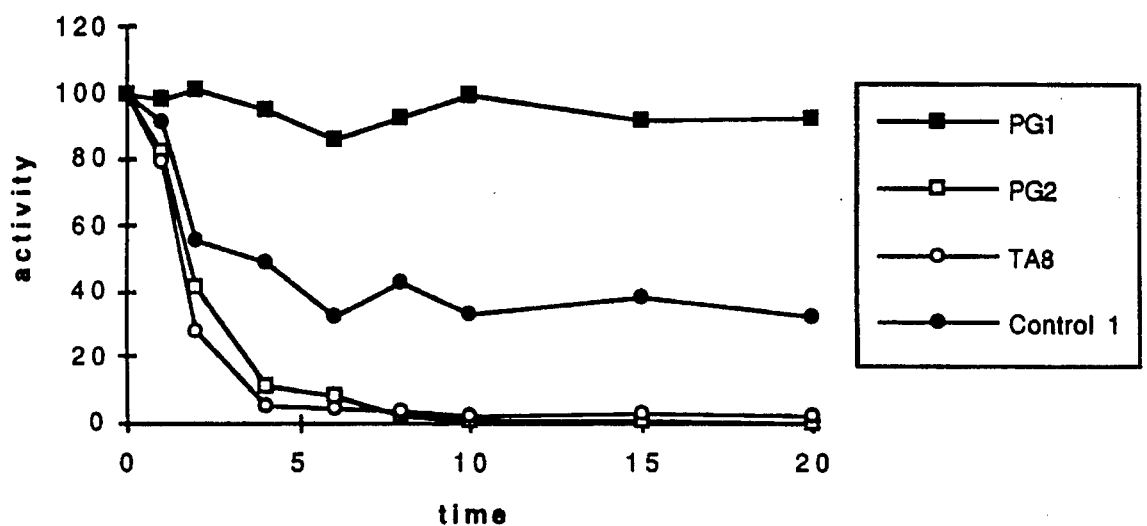
FIGS. 8 and 9 are graphical representations of data on heat stability of PG activity in control and transgenic plants.
Figure 9:
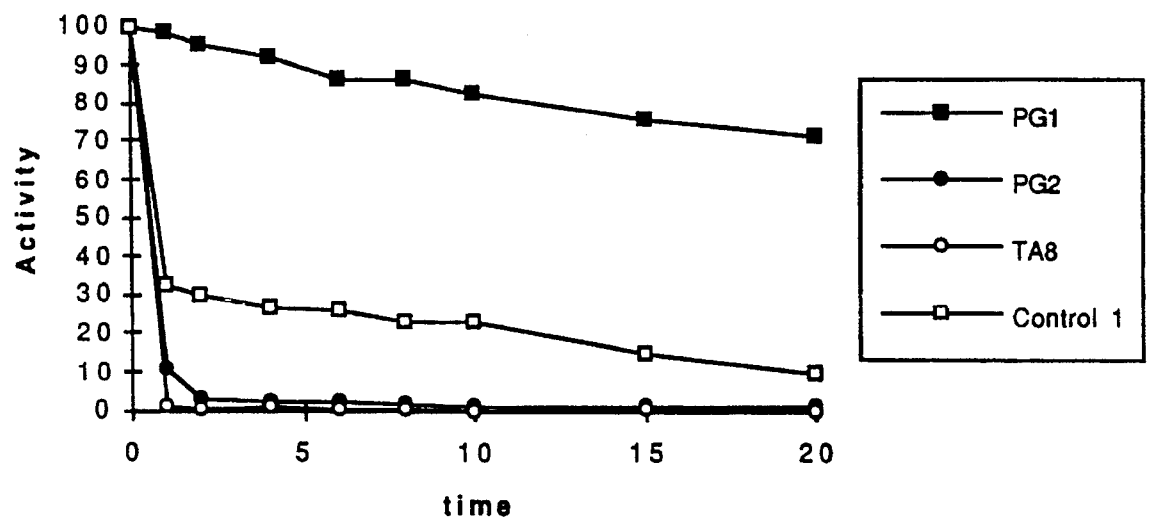

The heat stability of PG activity in fruit extract was also compared for experimentals and controls. In FIG. 8, a graph of PG activity for control fruit versus TA8 fruit in a heat inactivation study at 63.5° C. is presented. In this experiment, and the next heat inactivation study as well, solutions of isolated PG1 and PG2 isoforms were treated in parallel for purposes of comparison. As FIG. 8 illustrates, the PG activity in TA8 fruit extract could be essentially extinguished by that treatment at 63.5° C. for ten minutes, a result not possible with wild type control fruit. As the data for PG1 and PG2 indicates, the clear explanation is the relative abundance of the two PG isoforms in the two fruit. FIG. 9 illustrates similar data for a heat inactivation study at 83.5° C., with similar results.

Breeding experiments were also conducted with the TA8 line. Over 60 TA8 F2 progeny were analyzed by Southern blotting which revealed Mendelian inheritance of the two antisense transgene copies as a single locus. Progeny plants were identified which were homozygous both for the presence of the transgene copies or their absence. The "wild type" TA8 progeny exhibited normal beta-subunit levels and normal soluble polyuronide levels while the homozygous transgene carrying TA8 progeny exhibited nearly undetectable levels of beta-subunit and greatly increased soluble polyuronide levels. Thus, inheritability of this phenotype as a single dominant locus was verified, establishing the possibility of transfer of this transgene allele with any desired tomato genetic background.

I claim:

1. A method of creating a transgenic tomato containing a lowered level of polygalacturonase isoform 1, comprising the steps of
   a) isolating a DNA sequence encoding at least a fifteen nucleotide portion of the tomato polygalacturonase beta-subunit;
   b) creating a genetic construction including, 5' to 3' a promoter effective in tomato cells, a coding sequence, and a transcriptional terminator, the coding region being derived from the DNA sequence, wherein the DNA sequence from step (a) is positioned so that an antisense polygalacturonase beta-subunit RNA is produced by the construction and wherein the antisense RNA is capable of inhibiting the polygalacturonase beta-subunit;
   c) transforming a tomato cell with the genetic construction, whereby the tomato cell produces a lowered level of polygalacturonase isoform 1; and
   d) regenerating a tomato plant from the transformed cell, wherein the tomato plant produces tomatoes.

2. The method of claim 1 wherein the transforming step is performed by Agrobacterium-mediated transformation.

3. The method of claim 1 wherein the DNA sequence in step (a) is SEQ ID NO: 6.

4. A genetic construction comprised of 5' to 3' in order:
   a) a promoter capable of expressing a downstream coding sequence in a tomato plant;
   b) a sequence encoding an RNA of at least fifteen nucleotides complementary to the mRNA of tomato polygalacturonase beta-subunit set forth in SEQ ID NO: 6; and c) a 3' termination sequence.

5. A bacteria containing the construction of claim 4.

6. A tomato plant cell containing the genetic construction of claim 4.

7. A genetic construction comprised of, 5' to 3' in order:
   a) a promoter capable of expressing a downstream coding sequence in a tomato plant;
   b) a DNA sequence encoding a tomato polygalacturonase beta-subunit protein; and
   c) a 3' termination, the construction capable of suppressing expression of an endogenous beta-subunit gene when transformed into tomato plants.

8. A bacteria containing the construction of claim 7.

9. A tomato plant cell containing the construction of claim 7.

10. A transgenic tomato plant comprising in its genome a foreign genetic construction comprising 5' to 3' a promoter effective in tomato, a coding region encoding an RNA of at least 15 nucleotides complementary to the mRNA of the tomato polygalacturonase beta-subunit gene, and a transcriptional terminator, the genetic construction effective in vivo in the tomato fruit to lower the level of production of the polygalacturonase beta-subunit protein.

11. Seed of the tomato plant of claim 10.

12. Fruit of the tomato plant of claim 10.

13. The transgenic tomato plant of claim 10 wherein the tomato polygalacturonase beta-subunit gene is that set forth in SEQ ID NO: 6 above.

14. A genetically altered tomato plant wherein less than 1% of the total cellular polygalacturonase activity comprises polygalacturonase isoform 1.

15. Seed of the tomato plant of claim 14.

16. Fruit of the tomato plant of claim 14.

17. A transgenic tomato plant comprising in its genome a foreign genetic construction comprising, 5' to 3', a promoter effective in tomato, a coding region encoding tomato polygalacturonase beta-subunit, and a transcriptional terminator, the foreign genetic construction effective in the tomato fruit to cause suppression of the expression of endogenous polygalacturonase beta-subunit expression.

18. Seed of the tomato plant of claim 17.

19. Fruit of the tomato plant of claim 17.

20. The transgenic tomato plant of claim 17 wherein the coding region is from SEQ ID NO: 6.

21. Tomato fruit from a transgenic tomato plant, the fruit comprising in its tissue a level of polygalacturonase isoform 1 protein that is less than 1% of the level of total polygalacturonase activity in the tissue.

22. Tomato fruit from a transgenic tomato plant, the fruit comprising an altered polygalacturonase activity in its tissue, the altered activity being such that the enzymatic polygalacturonase activity in the tissue can be substantially eliminated by heat treatment at 63.5° C. for ten minutes.

23. Tissue extract from the fruit of claim 22.

24. The method of claim 1 wherein the step (a) DNA sequence comprises the 3' end of the tomato polygalacturonase beta-subunit.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Lycopersicon esculentum ( x i ) SEQUENCE DESCRIPTION: SEQ ID NO:1:

Asn  Gly  Asn  Gly  Ala  Asn  Gly  Gln  Xaa  Val
    1                      5                            10

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Lycopersicon esculentum ( x i ) SEQUENCE DESCRIPTION: SEQ ID NO:2:

Ala  Asn  Ala  Gly  Asp  Gln  Tyr
    1                      5

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: YES ( i v ) ANTI-SENSE: NO ( x i ) SEQUENCE DESCRIPTION: SEQ ID NO:3:

GGNAAYGGNG CNAAYGG                                                                                      17

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: YES ( i v ) ANTI-SENSE: NO ( x i ) SEQUENCE DESCRIPTION: SEQ ID NO:4:

AAYGCNGGNG AYCARTA                                                                                      17

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: YES ( i v ) ANTI-SENSE: YES ( x i ) SEQUENCE DESCRIPTION: SEQ ID NO:5:

ATRTCNCCRC TRTGYTTYTC                                                                                   20

( 2 ) INFORMATION FOR SEQ ID NO:6:

( i ) SEQUENCE CHARACTERISTICS:
        ( A ) LENGTH: 2192 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Lycopersicon esculentum ( x i ) SEQUENCE DESCRIPTION: SEQ ID NO:6:

```
TCTCTCTCTT   CATCTCTGTT   TCACACCAAA   GAAATGCACA   CTAAAATTCA   TCTTCCTCCC      60
TGCATCTTAC   TTCTTCTTCT   GTTCTCACTA   CCATCTTTCA   ATGTTGTTGT   AGGTGGAGAT     120
GGTGAATCTG   GTAACCCATT   TACACCCAAA   GGTTATCTGA   TTAGGTACTG   GAAGAAACAA     180
ATCTCAAATG   ACTTACCAAA   GCCATGGTTT   CTTCTGAACA   AGGCATCTCC   ATTGAATGCT     240
GCACAATATG   CAACTTACAC   TAAACTTGTT   GCTGATCAAA   ATGCACTCAC   CACACAGCTC     300
CATACCTTTT   GCTCTTCAGC   AAATCTCATG   TGTGCACCAG   ATCTGTCACC   AAGTCTTGAA     360
AAACACAGTG   GAGATATCCA   TTTTGCCACT   TACAGTGACA   AAAACTTTAC   CAATTATGGA     420
ACCAATGAAC   CTGGAATTGG   AGTTAACACT   TTCAAGAACT   ACTCTGAAGG   AGAAAACATC     480
```

```
CCTGTAAATT  CTTTCAGGCG  ATATGGTAGA  GGTTCTCCCC  GTGACAATAA  ATTTGACAAT     540
TACGCCTCTG  ATGGCAATGT  TATTGACCAA  AGTTTCAATT  CCTATAGCAC  AAGTACTGCT     600
GGAGGTTCAG  GCAAATTCAC  AAATTACGCG  GCGAATGCCA  ATGACCCAA   TCTGCATTTC     660
ACTTCCTATT  CCGATCAAGG  AACAGGAGGT  GTACAGAAAT  TCACAATATA  CTCACAAGAA     720
GCCAATGCTG  GTGACCAGTA  TTTCAAAAGT  TACGGCAAAA  ATGGGAATGG  TGCTAATGGT     780
GAATTCGTCA  GCTATGGAAA  TGACACAAAT  GTTATCGGCT  CAACATTTAC  AAATTATGGT     840
CAGACAGCAA  ATGGGGGAGA  CCAAAAATTC  ACATCTTATG  GTTTCAACGG  CAATGTTCCT     900
GAAAATCATT  TCACCAACTA  TGGTGCTGGA  GGTAATGGTC  CATCTGAAAC  TTTTAATAGT     960
TACAGAGATC  AATCGAATGT  TGGAGATGAC  ACATTCACTA  CCTATGTTAA  GGATGCAAAT    1020
GGCGGTGAAG  CGAATTTCAC  CAACTATGGT  CAATCATTCA  ATGAAGGTAC  TGATGTATTC    1080
ACTACTTACG  GCAAAGGGGG  TAATGACCCA  CATATCAATT  TCAAAACTTA  CGGAGTTAAC    1140
AACACTTTCA  AAGATTATGT  CAAAGATACT  GCTACATTTT  CCAATTACCA  CAACAAAACT    1200
TCCCAAGTTT  TAGCATCGTT  GATGGAGGTC  AACGGTGGTA  AAAAGGTGAA  TAACCGGTGG    1260
GTTGAGCCCG  GAAAGTTTTT  CCGGGAGAAG  ATGTTGAAGA  GTGGTACAAT  CATGCCTATG    1320
CCAGATATAA  AGGATAAGAT  GCCTAAAAGG  TCCTTTTTGC  CCCGGGTGAT  TGCTTCCAAA    1380
TTACCATTTT  CTACTTCAAA  AATTGCTGAG  CTGAAGAAAA  TCTTCCACGC  CGGTGATGAG    1440
TCTCAGGTGG  AGAAGATGAT  CGGCGATGCA  TTGAGTGAGT  GTGAAAGAGC  ACCGAGCGCC    1500
GGTGAGACGA  AACGATGTGT  TAATTCAGCT  GAAGATATGA  TTGATTTCGC  AACATCAGTG    1560
TTGGGTCGAA  ACGTCGTCGT  TCGAACGACT  GAGGATACAA  AAGGATCAAA  TGGGAATATC    1620
ATGATTGGAT  CAGTCAAAGG  AATCAACGGT  GGAAAAGTTA  CTAAATCAGT  ATCATGTCAT    1680
CAAACGCTGT  ACCCTTACTT  ACTGTATTAC  TGTCATTCGG  TTCCTAAAGT  CCGGGTCTAC    1740
GAAGCGGATA  TTTTGGACCC  GAATTCAAAG  GTTAAGATCA  ATCATGGTGT  CGCGATTTGC    1800
CACGTGGATA  CATCTTCATG  GGGACCGAGT  CACGGAGCGT  TTGTCGCACT  CGGGTCGGGA    1860
CCCGGGAAAA  TAGAAGTTTG  TCATTGGATC  TTTGAGAATG  ATATGACTTG  GGCAATTGCT    1920
GATTGAGAAA  AAAAAAAGAA  ATGAAATAAT  ATGCAAAATT  TCTAATTCGG  GTCGAACCGG    1980
GTGTGTTACA  AGAAGAAGAA  AAAAGGTACC  ACTGGTTTGA  CTTTTATAGT  AATTATTATT    2040
ATTATAGTCT  TAATTTATAT  TTGAGTAAT   TTCGTGTAA   GTTTCTCTTT  GCCTTCATTA    2100
AGTATGAATG  GCTATCAATT  TACACTATTT  GTTATGTAAT  CATTTATTG   TTGACTCATA    2160
TTTGAGCAAG  GTAATGTAGT  TATTGCCAGA  TG                                    2192
```